United States Patent [19]
Habuchi et al.

[11] Patent Number: 5,834,282
[45] Date of Patent: Nov. 10, 1998

[54] HEPARAN SULFATE 6-O-SULFOTRANSFERASE

[75] Inventors: Hiroko Habuchi; Osami Habuchi; Koji Kimata, all of Nagoya, Japan

[73] Assignee: Seikagaku Kogyo Kabushiki Kaisha, Tokyo, Japan

[21] Appl. No.: 505,813

[22] Filed: Jul. 21, 1995

[30] Foreign Application Priority Data

Jul. 22, 1994 [JP] Japan ................................ 6-171379

[51] Int. Cl.$^6$ .............................. C12N 9/10; C12P 19/26
[52] U.S. Cl. ......................... 435/193; 435/84; 435/101; 435/130; 435/183
[58] Field of Search ................................ 435/193, 183, 435/84, 101, 814, 130

[56] References Cited

FOREIGN PATENT DOCUMENTS

WO25659  12/1993  WIPO .

OTHER PUBLICATIONS

I. Jacobsson et al., "Biosynthesis of Heparin", The Journal of Biological Chemistry, Jun. 1980, vol. 255, No. 11, pp. 5094–5100.

D. Göhler et al., "Purification and Characterization of 3'—phosphoadenylylsulfate: N–desulfoheparan sulfate sulfotransferase from arterial tissue" European Journal of Biochemistry, vol. 138, 1984, pp. 301–308.

H. Inoue et al., "Glycosaminoglycan Sulfotransferases in Human and Animal Sera", The Journal of Biological Chemistry, Apr. 1986, vol. 261, No. 10, pp. 4460–4469.

E. Brandan et al., "Purification of Rat Liver N–Heparan–sulfate Sulfotransferase", The Journal of Biological Chemistry, Feb. 1988, vol. 263, No. 5, pp. 2417–2422.

M. Kusche et al., "Biosynthesis of Heparin; O–Sulfation of the Antithrombin–Binding Region", The Journal of Biological Chemistry, Oct. 1988, vol. 263, No. 30, pp. 15474–15484.

M. Kushce et al., "Biosynthesis of Heparin; O–Sulfation of D–Glucuronic Acid Units", The Journal of Biological Chemistry, Sep. 1990, vol. 265, No. 26, pp. 15403–15409.

Translation of "Sulfotransferases in Tissues" in Shin–Seikagaku–Jikken–Koza, 3, p. 194, published by Tokyo–Kagaku–Dojin, Apr. 1991.

M. Kushce et al., "Biosynthesis of Heparin; Enzymatic Sulfation of Pentasaccharides", The Journal of Biological Chemistry, Apr. 1991, vol. 266, No. 12, pp. 7400–7409.

I. Pettersson et al., "Biosynthesis of Heparin; Purification of A 110–kDa Mouse Mastocytoma Protein Required for Both Glucosaminyl N–Deacetylation and N–Sulfation", The Journal of Biological Chemistry, May 1991, vol. 266, No. 13, pp. 8044–8049.

H. Wlad et al., "Partial Purification of O–Sulfotransferases Involved in the Biosynthesis of Heparin", Glycoconjugate Journal, 1991 vol. 8, pp. 200–201.

Translation of "Isolating and Refining the Heparan Sulfate 6–Sulfated Enzyme" The Journal of Biochemistry issued by Japanese Biochemical Society, vol. 66, No. 7, 1994, p. 1043.

H. Wlad et al., "Biosynthesis of Heparin; Different Molecular Forms of O–Sulfotransferases", The Journal of Biological Chemistry, Oct. 1994, vol. 269, No. 40, pp. 24538–24541.

H. Habuchi et al., "Purification and Characterization of Heparan Sulfate 6–Sulfotransferase from the Culture Medium of Chinese Hamster Overy Cells", The Journal of Biological Chemistry, Feb. 1995, vol. 270, No. 8, pp. 4172–4179.

Hanna Wlad et al., "Partial Purification of O–Sulfotransferases Involved in the Biosynthesis of Heparin", Glycoconjugate Journal, pp. 200–201, vol. 8, No. 3, Jun. 1991.

Hanna Wlad et al., "Biosynthesis of Heparin", Journal of Biological Chemistry, pp. 24538–24541, vol. 269, No. 40, Oct. 1994.

Hiroko Habuchi et al., "Purification and Characterization of Heparan Sulfate 6–Sulfotransferase from the Culture Medium of Chinese Hamster Ovary Cells", Journal of Biological Chemistry, pp. 4172–4179, vol. 270, No. 8, Feb. 1995.

*Primary Examiner*—Blaine Lankford
*Attorney, Agent, or Firm*—Knobbe, Martens, Olson & Bear, LLP

[57] ABSTRACT

The present invention provides a heparan sulfate 6-O-sulfotransferase for selectively introducing sulfate group into hydroxyl group at C-6 of glucosamine of heparin and heparan sulfate, having the following properties: (i) sulfate group is selectively transferred from a sulfate group donor to hydroxyl group at C-6 of N-sulfoglucosamine residue; (ii) sulfate group is transferred to CDSNS-heparan, but sulfate group is not transferred to chondroitin and chondroitin-4-sulfate; (iii) optimum reaction pH is in a range of pH 6-7; (iv) optimum ionic strength is in a range of 0.1–0.3 M (in the case of sodium chloride); and (v) the enzyme activity is inhibited by dithiothreitol and adenosine-3',5'-diphosphate, and activated by protamine.

11 Claims, 12 Drawing Sheets

HEPARAN SULFATE 6-O-SULFOTRANSFERASE

BACKGROUND OF THE INVENTION

Technical Field

The present invention relates to a novel sulfotransferase, and in particular relates to a heparan sulfate 6-O-sulfotransferase, which selectively transfers sulfate group to hydroxyl group at C-6 of N-sulfoglucosamine contained in heparin and heparan sulfate.

BACKGROUND ART

Heparin and heparan sulfate are polysaccharide belonging to glycosaminoglycan. Heparin and heparan sulfate have similar fundamental sugar chain backbones, both of which are generated by synthesis of a chain through 1→4 bond of N-acetylglucosamine (GlcNAc) and glucuronic acid (GlcA) followed by processing, however, the degree of processing is different between the both. Namely, although the both are charged strongly negatively, heparin contains larger amounts of N-sulfated glucosamine, 6-O-sulfated glucosamine, and 2-O-sulfated iduronic acid. Heparan sulfate and heparin are present in tissues in a form of proteoglycan in which the sugar chain covalently binds to a core protein, as in the same manner as other glycosaminoglycans.

Heparin proteoglycan has been found in secreted granules of mast cells and halophilic cells, and considered to contribute to packaging of histamine and basic protease. Heparan sulfate proteoglycan is widely distributed over extracellular matrices and cell surfaces, and known to concern various functions such as differentiation, growth and movement of cells, and anticoagulation.

By the way, basic fibroblast growth factor (bFGF) is a protein that strongly facilitates growth of an extremely wide variety of cells such as those of vascular system, connective tissue system, brain nervous system, and immune system. On the other hand, acidic fibroblast growth factor (aFGF) is a protein that is often found in nervous system such as brain and retina. Since aFGF binds to a cell surface receptor common to bFGF, the both are considered to have essentially the same acting mechanism.

It has been revealed that aFGF and bFGF strongly bind to a sugar chain moiety of heparan sulfate proteoglycan incorporated in extracellular matrices or basement membranes of tissues. Recently, it has been suggested that a heparin or heparan sulfate chain is essential for bFGF to bind to a high affinity receptor (Yayon, A. et al., Cell, 64, 841–848 (1991)); Rapraeger, A. C., Science, 252, 1705–1708 (1991)). Further, it has been suggested that the bFGF activity also requires binding of these sugar chains to the high affinity receptor itself (Kan, M. et al., Science, 259, 1918–1921 (1993); Guimond, S. et al., J. Biol. Chem., 268, 23906–23914 (1993)). The present inventors have demonstrated that a special structural domain concerning binding to bFGF is present on the chain of heparan sulfate, and that the binding of bFGF to the chain of heparan sulfate greatly affects metabolism of bFGF (Habuchi, H. et al. (1992) Biochem. J., 285, 805–813). It is known that binding of bFGF requires the presence of 2-O-sulfate group of iduronic acid residue and N-sulfated glucosamine residue on the heparan sulfate chain (Habuchi, H. et al., Biochem. J., 285, 805–813 (1992); Turnbull, J. E. et al., J. Biol. Chem., 267, 10337–10341 (1992)).

It has been reported that heparan sulfate relevant to formation of highly organized basement membrane has a high degree of sulfation at C-6 of glucosamine residue (Nakanishi, H. et al., Biochem. J., 288, 215–224 (1992)). It has been also reported that the affinity of heparin to fibronectin increases in accordance with the molecular weight and the sulfate content of heparin (Ogamo, A. et al., Biochim. Biophys. Acta, 841, 30–41 (1985)). It is also known that the higher the ability of transposition of a cell strain clone originating from Lewis-lung-carcinoma is, the more the content of 6-O-sulfation in synthesized heparan sulfate is (Nakanishi, H., Biochem. J., 288, 215–224 (1992)), and that the degree of sulfation of heparan sulfate decreases in accordance with malignant alteration. Accordingly, it is considered that sulfation plays an important role for expression of physiological activities of metastasis and heparan sulfate.

Considering the importance of sulfation in expression of physiological activities of heparin and heparan sulfate, a method for sulfating a specific site of heparin and heparan sulfate may be essential for analysis of physiological activities and modification of functions of heparin and heparan sulfate. A method for chemically introducing sulfate group selectively into N- and O-positions has been already reported (Shin-Seikagaku-Jikken-Koza (New Biochemical Experiment Course), 3, "Saccharides II", p324, published by Tokyo-Kagaku-Dojin). However, it requires complicated treatment operations, requires many kinds of reagents, and takes a long time. Thus a method for enzymatically introducing sulfate group has been demanded. A heparan sulfate (GlcN) 2-N-sulfotransferase has been isolated and purified as an enzyme for N-selectively introducing sulfate groups (Shin-Seikagaku-Jikken-Koza, 3, "Saccharides II", p194, published by Tokyo-Kagaku-Dojin). It has been also tried to isolate and purify an enzyme which transfers sulfate group selectively to C-6 of glucosamine of heparan sulfate (heparan sulfate (GlcNAc) 6-O-sulfotransferase). However, it was reported that the enzyme was contaminated with iduronic acid (IdoA) 2-O-sulfotransferase even after purification to a high degree, and the separation of the both was difficult (Wald, H. et al., Glycoconjugate J., 8, 200–201 (1991)).

Considering the importance of sulfation in expression of physiological activities of heparin and heparan sulfate, it is very important to develop a method for transferring sulfate group to heparin and heparan sulfate not only to study functional analysis of heparin and heparan sulfate but also to provide heparin and heparan sulfate for the purpose of creation of pharmaceuticals having physiological activities preferable for human. Especially, heparan sulfate (GlcN) 2-N-sulfotransferase has now been isolated, and thus isolation and purification of heparan sulfate (GlcN) 6-O-sulfotransferase have been waited for.

SUMMARY OF THE INVENTION

The present invention has been made taking the aforementioned viewpoints into consideration, an object of which is to provide a heparan sulfate 6-O-sulfotransferase which selectively introduces sulfate group into C-6 of glucosamine of heparin and heparan sulfate.

The present inventors have diligently searched for an enzyme which selectively transfers sulfate group to hydroxyl group at C-6 of N-sulfoglucosamine contained in heparin and heparan sulfate, that is heparan sulfate 6-O-sulfotransferase (hereinafter referred to as "heparan sulfate 6-sulfotransferase" or the enzyme of the present invention), succeeded in isolation and purification of the enzyme, confirmed that the enzyme selectively transfers sulfate group to hydroxyl group at C-6 of N-sulfoglucosamine of heparin and heparan sulfate, and arrived at the present invention.

Namely, the present invention lies in a heparan sulfate 6-sulfotransferase having the following physical and chemical properties:

(i) action: sulfate group is selectively transferred from a sulfate group donor to hydroxyl group at C-6 of N-sulfoglucosamine residue;

(ii) substrate specificity: sulfate group is transferred to heparan sulfate or CDSNS-heparin completely desulfated and N-resulfated heparin, but sulfate group is not transferred to chondroitin and chondroitin-4-sulfate;

(iii) optimum reaction pH: pH 6–7;

(iv) optimum ionic strength: 0.1–0.3M (in the case of sodium chloride); and (v) inhibition and activation: the enzyme is inhibited by dithiothreitol and adenosine-3',5'-diphosphate, and activated by protamine.

The present invention also provides a method of producing heparan sulfate 6-O-sulfotransferase, comprising the steps of cultivating cell lines selected from fibroblast cells originating from ovary tissue of Chinese hamster, cells originating from mouse breast carcinoma, and cells originating from human osteosarcoma in an appropriate medium in which the cells can grow, secreting and accumulating the aforementioned heparan sulfate 6-O-sulfotransferase in the medium, and collecting the heparan sulfate 6-O-sulfotransferase from the medium.

The enzyme of the present invention is conveniently referred to as "heparan sulfate 6-O-sulfotransferase" or "heparan sulfate 6-sulfotransferase". However, it is not meant that the substrate of the enzyme is limited to heparan sulfate. The enzyme has an activity to transfer sulfate group also on CDSNS-heparin. Unmodified heparin usually has sulfate groups at C-6 of almost all glucosamine residues. However, there exists heparin having hydroxyl groups at C-6 of a few glucosamine residues. The enzyme of the present invention also transfers sulfate group to C-6 of glucosamine residue of such heparin. Therefore, in this specification, ordinary heparin as well as modified heparin having sulfate group at C-2 and hydroxyl group at C-6 of glucosamine residue is occasionally referred to simply as "heparin".

<1> Heparan sulfate 6-sulfotransferase of the present invention

The enzyme of the present invention is an enzyme which has been isolated for the first time according to the present invention, and has the following physical and chemical properties.

(i) Action

Heparan sulfate or heparin having sulfate group at C-2 and hydroxyl group at C-6 of glucosamine residue is used as an acceptor. Sulfate group is selectively transferred from a sulfate group donor to hydroxyl group at C-6 of N-sulfoglucosamine residue thereof, while it is scarcely transferred to uronic acid residue. The sulfate group donor is preferably exemplified by active sulfate (3'-phosphoadenosine 5'-phosphosulfate; hereinafter referred to as "PAPS").

(ii) Substrate specificity

Sulfate group is transferred to heparan sulfate or CDSNS-heparin, but sulfate group is not transferred to chondroitin and chondroitin-4-sulfate. Sulfate group is scarcely transferred to heparin or heparan sulfate having no sulfate group at C-2 of glucosamine such as NDS-heparin (N-desulfated heparin). Therefore, it may be necessary for the sulfate group acceptor for the enzyme of the present invention that C-2 of glucosamine residue of mucopolysaccharide is sulfated.

(iii) Optimum reaction pH

The enzyme of the present invention has a high activity to transfer sulfate group in a range of pH 6–7, especially in the vicinity of pH 6.3. Little activity is provided at pH 4.7 or below.

(iv) Optimum ionic strength

The activity of the enzyme of the present invention increases as the ionic strength increases. In the case of NaCl, the highest activity is presented at 0.1–0.3M, especially in the vicinity of 0.15M. The activity gradually decreases when the concentration of NaCl increases exceeding the aforementioned range. The activity becomes extremely low at 0.5M.

(v) Inhibition and activation

The activity of the enzyme of the present invention is inhibited by dithiothreitol (DTT) and adenosine-3',5'-diphosphate (3',5'-ADP), and activated by protamine. The activity is reduced to a half in the presence of 1 mM DTT. The activity increases about 10-fold in the presence of protamine of more than about 0.025 mg/ml as compared with the activity in the absence of protamine.

(vi) Michaelis constant

The enzyme of the present invention has a Michaelis constant (Km) of $4.4 \times 10^{-7}$M for PAPS when heparan sulfate is used as a sulfate group acceptor and PAPS is used as a donor.

(vii) Other properties

As a result of analysis of an active fraction of the enzyme of the present invention obtained from a culture liquid of CHO cell by means of SDS-polyacrylamide gel electrophoresis, bands having molecular weights of 45 kDa and 52 kDa have been found. Results of determination of amino acid sequences at N-terminals of these proteins are shown in SEQ ID NOS. 1 and 2, respectively. As a result, it has been found that the N-terminal sequences of these proteins are extremely similar, suggesting that they are correlated. However, it is not clarified which of these proteins is the enzyme of the present invention, or whether or not the both are the enzyme of the present invention. In any case, the physical and chemical properties of the enzyme of the present invention described above have been determined by using the fraction containing the both proteins of 45 kDa and 52 kDa. The mobility of the both proteins on electrophoresis was not affected by the presence of mercaptoethanol.

As a result of analysis of the enzyme of the present invention after an N-glycanase (produced by Genzyme Co.) treatment by means of SDS-polyacrylamide gel electrophoresis, the aforementioned bands of 45 kDa and 52 kDa have disappeared, while bands of 38 kDa and 43 kDa have newly appeared. According to this fact, it is suggested that these proteins are glycoproteins containing more than 15% of sugar.

The activity to transfer sulfate group of the enzyme of the present invention can be measured by using [$^{35}$S]-PAPS as a sulfate group donor and heparin or heparan sulfate as a sulfate group acceptor, allowing the enzyme of the present invention to act on them, and counting radioactivity of [$^{35}$S] incorporated into heparin or heparan sulfate. In this measurement, it is preferable that pH of a reaction solution is 6–7, the ionic strength is about 0.15M, and protamine is added in an amount more than 0.025 mg/ml. Specifically, for example, a reaction solution (50 μl) containing 2.5 μmol of imidazole hydrochloride (pH 6.8), 3.75 μg of protamine hydrochloride, 25 nmol of CDSNS-heparin (completely desulfated and N-resulfated heparin: heparin obtained by desulfation of N,O-sulfate groups followed by N-resulfation), 50 pmol of [$^{35}$S]-PAPS (about 5×10$^5$ cpm), and the enzyme is kept at a temperature of 37° C. for 20 minutes, followed by heating at 100° C. for 1 minute to stop the reaction. Subsequently, 0.1 μmol of chondroitin sulfate A is added as a carrier, and then $^{35}$S-glycosaminoglycan is precipitated by adding cold ethanol containing 1.3% potassium acetate in an amount three times the reaction solution. Further, [$^{35}$S]-PAPS and its degradation products are removed by desalting, liquid scintillator is added, and radioactivity of [$^{35}$S] is measured by using a liquid scintillation counter. In the present invention, an activity to transfer 1 pmol of sulfate group per 1 minute under the aforementioned condition is defined as an enzyme amount of 1 unit (U).

<2> Production method of the enzyme of the present invention

The enzyme of the present invention having the properties described above is obtained by cultivating cell line such as cell line originating from animals, for example, fibroblast cell originating from ovary tissue of Chinese hamster, cell originating from mouse breast carcinoma, or cell originating from human osteosarcoma, specifically CHO cell (for example, ATCC CCL61 and the like), FM3A cell (JCRB0701 from JCRB Cell Bank of National Institute of Hygienic Sciences and the like), or MG63 cell (for example, ATCC CRL1427 and the like) in an appropriate medium in which the cells can grow, secreting and accumulating the enzyme in the medium, and collecting it from the medium. Among the cell lines described above, CHO cell is preferable from a viewpoint of yield of the enzyme of the present invention. The enzyme of the present invention may be obtained from cultured cells other than those described above, however, the cell lines described above are preferred because of good growth properties and possibility of cultivation in a serum-free medium. The enzyme of the present invention can be also extracted from cultured cells themselves. The enzyme of the present invention may be used as a crude enzyme when other contaminating sulfotransferase activities can be effectively suppressed.

The medium to be used for the cultivation of the cell lines described above is not specifically limited, however, it is preferable to use a serum-free medium. If the cultivation in a serum-free medium is possible, the protein concentration in the medium can be made extremely low, which makes it easy to purify the enzyme of the present invention from the medium. A commercially available serum-free medium such as Cosmedium-001 medium (Cosmo Bio) may be used as the serum-free medium.

When the aforementioned CHO cell or the like are cultivated, they may be proliferated to a required number of cells by using Dulbecco's Modified Eagle Medium or the like, and the medium may be changed to the serum-free medium to continue cultivation.

In the present invention, for example, it is preferable that the cell lines are cultivated for more than 10 days while exchanging the medium every second day, and used media are combined to collect the enzyme of the present invention. Therefore, in order to prevent cells from peeling off from a cultivation vessel such as a dish during the exchange of the medium, it is preferable to add ascorbic acid in an amount of about 50 μg/ml to enhance synthesis and deposition of collagen as a cell-adhesion substance. In order to avoid growth of microorganisms, it is preferable to add antibiotics such as penicillin and streptomycin to the medium. When the medium as described above is used to conduct cultivation in the same manner as ordinary cultured cells by using roller bottles or dishes, the enzyme of the present invention is secreted into the medium.

The enzyme of the present invention can be purified from the medium by means of affinity chromatography using a Heparin-Sepharose CL-6B (produced by Pharmacia) column, a 3',5'-ADP-agarose column and the like, or Resource Q (produced by Pharmacia) column chromatography. Especially, 3',5'-ADP-agarose column chromatography is effective. Additionally, the enzyme can be purified by using known enzyme purification methods such as ion exchange chromatography, gel filtration, electrophoresis, and salting out, if necessary.

The enzyme of the present invention may be also obtained by using transformed cells obtained by isolating a gene coding for the enzyme of the present invention from the cultured cells described above, and introducing it into other cultured cells or microbial cells.

The enzyme of the present invention has enabled enzymatic selective introduction of sulfate group into C-6 of N-sulfoglucosamine contained in heparin and heparan sulfate. The heparan sulfate 6-sulfotransferase selectively introduces sulfate group into C-6 of N-sulfoglucosamine of heparin and heparan sulfate extremely strictly. Accordingly, it is expected to exploit the enzyme for reagents useful for studies such as functional analysis of heparin and heparan sulfate.

Considering creation of heparin and heparan sulfate having new physiological activities unknown at present and application as pharmaceuticals by using the enzyme of the present invention, it can be expected to create heparin or heparan sulfate having physiological activities preferable for human. Since it is known that the degree of sulfation of heparan sulfate decreases in accordance with malignant alteration, it is also expected to enable the amount of the enzyme to be related to malignant alteration by producing an antibody against the enzyme of the present invention and detecting the enzyme of the present invention in tissues.

Description of Preferred Embodiments

Figure 1:
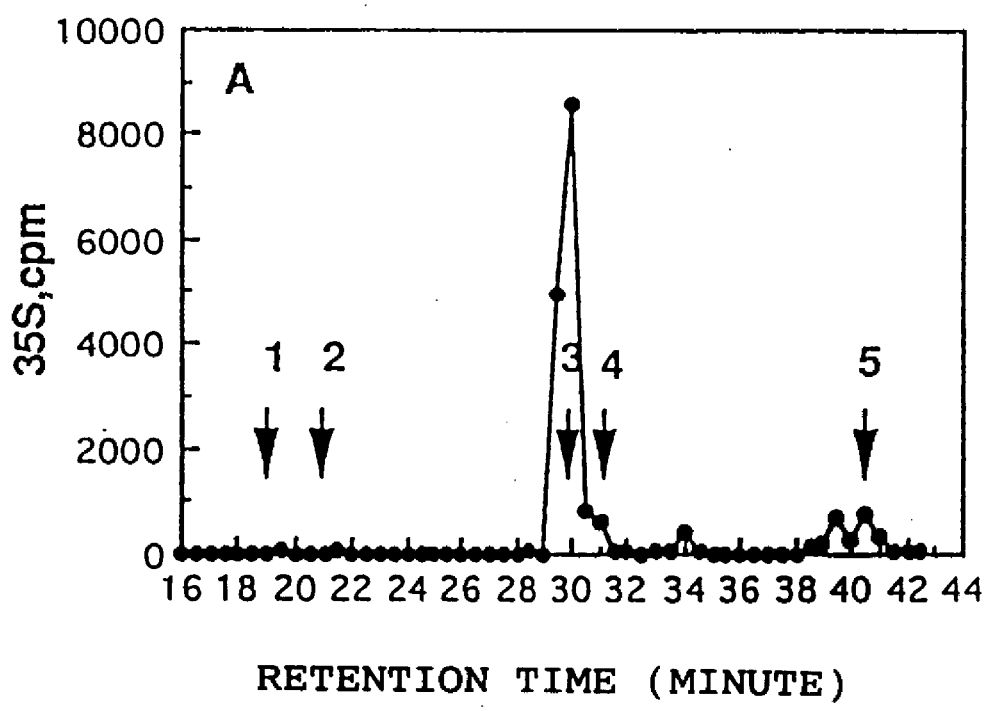
FIG. 1 shows HPLC chromatograms of heparitinase digests of products of the reaction to transfer sulfate group to CDSNS-heparin by heparan sulfate O-sulfotransferase secreted by CHO cell (A) and FM3A cell (B).
Figure 1:
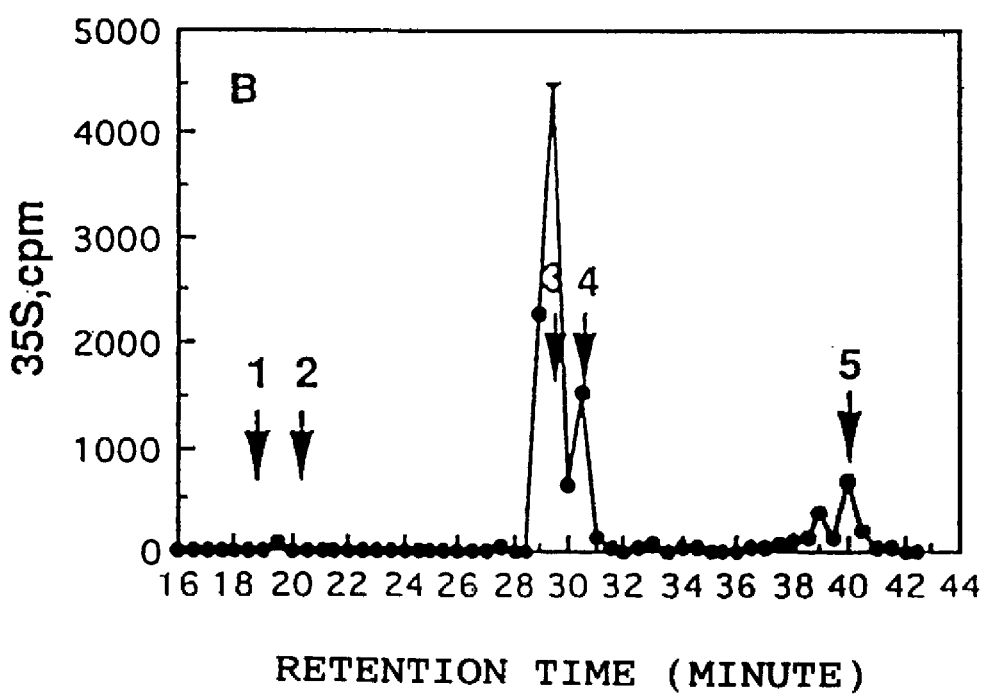

Embodiments of the present invention will be described below.

<1> Reagents and measurement of enzyme activity of heparan sulfate 6-sulfotransferase (1) Reagents Available sources and methods for obtaining reagents and samples used in this embodiment are described below.

[$^{35}$S]-H$_2$SO$_4$ was purchased from Japan Radioisotope Association. Dulbecco's Modified Eagle Medium, trypsin (type III from bovine spleen), PAPS, 3',5'-ADP-agarose, and heparin were purchased from Sigma. Cosmedium-001 medium was purchased from Cosmo Bio. Fast desalting column, and Heparin-Sepharose CL-6B column were purchased from Pharmacia-LKB. PAMN column (silica column with bound polyamine) was purchased from YMC. Chondroitinase ABC, heparitinase I, II, III, chondroitin sulfate A (from shark cartilage, 4S/6S:80/20), CDSNS-heparin (completely desulfated and N-resulfated heparin: heparin obtained by desulfation of N,O-sulfate groups followed by N-resulfation), and unsaturated disaccharide kit from glycosaminoglycan were purchased from Seikagaku Corporation. [$^{35}$S]-PAPS was prepared in accordance with a method described by Delfert, D. M. and Conrad, E. H. (1985) in *Anal. Biochem.*, 148, 303–310. Chondroitin (from squid skin) was prepared in accordance with a method described by Habuchi, O. and Miyata, K. (1980) in *Biochim. Biophys. Acta*, 616, 208–217.

(2) Measurement of heparan sulfate 6-sulfotransferase

The enzyme activity was measured in accordance with a method described below in purification steps of the heparan sulfate 6-sulfotransferase, analysis of properties of the enzyme and so on.

An enzyme reaction solution was 50 μl which contained 2.5 μmol of imidazole hydrochloride (pH 6.8), 3.75 μg of protamine hydrochloride, 25 nmol of CDSNS-heparin, 50 pmol of [$^{35}$S]-PAPS (about 5×10$^5$ cpm), and the enzyme. This reaction solution was kept at a temperature of 37° C. for 20 minutes, followed by heating at 100° C. for 1 minute to stop the reaction. Subsequently, 0.1 μmol of chondroitin sulfate A was added as a carrier, and then $^{35}$S-glycosaminoglycan was precipitated by adding cold ethanol containing 1.3% potassium acetate in an amount three times the reaction solution. Further, [$^{35}$S]-PAPS and its decomposed products were completely separated by using a fast desalting column as described before (Habuchi, O. et al., (1993) *J. Biol. Chem.*, 268, 21968–21974). Liquid scintillator (Ready Safe Scintillator, produced by Beckman) was mixed therewith, and radioactivity was measured by using a liquid scintillation counter to calculate the amount of transferred sulfate group. An activity to transfer 1 pmol of sulfate group per 1 minute under the aforementioned condition was defined as an enzyme amount of 1 unit (U).

The activity of chondroitin sulfotransferase was also measured in the same manner.

(3) Measurement of contents of galactosamine and glucosamine of glycosaminoglycan Contents of galactosamine and glucosamine of glycosaminoglycan were measured by an Elson-Morgan method after hydrolyzing the glycosaminoglycan in 6M HCl at 100° C. for 4 hours.

<2> Analysis of heparan sulfate O-sulfotransferase secreted by various cultured cells CHO cell (ATCC CCL61), FM3A cell (JCRB 0701), and MG63 cell (ATCC CRL1427) were inoculated at a density of 3×10$^6$ cells/dish respectively, and cultivated for 2 days in 10 ml of Dulbecco's Modified Eagle Medium containing 10% fetal bovine serum, 10 mM HEPES (N-2-hydroxyethylpiperazine-N'-2-ethanesulfonic acid), pH 7.2, 50 units/ml of penicillin, and 50 μg/ml of streptomycin. Subsequently, cells were cultivated for 48 hours by using 10 ml of Cosmedium-001 medium containing 50 μg/ml of ascorbic acid and 10 mM HEPES, pH 7.2. Each of the media was applied to a Heparin-Sepharose column (1 ml) equilibrated with buffer A (10 mM Tris-HCl, pH 7.2, 10 mM MgCl$_2$, 2 mM CaCl$_2$, 20% glycerol, 0.1% Triton X-100) containing 0.15M NaCl, washed with buffer A containing 0.15M NaCl, and eluted with buffer A containing 1.0M NaCl. The eluted fraction was used as a crude enzyme of heparan sulfate O-sulfotransferase to make measurement using CDSNS-heparin as an acceptor. The heparan sulfate O-sulfotransferase activity per 2×10$^7$ cells of each of the cells is shown in Table 1. As a result, a culture liquid of the CHO cell presented the highest sulfotransferase activity.

TABLE 1

| Cultured cells | Heparan sulfate O-sulfotransferase activity |
|---|---|
| CHO | 7.74 |
| FM3A | 1.25 |
| MG63 | 1.31 |

A reaction product, which was obtained by maintaining a reaction solution containing CDSNS-heparin, [$^{35}$S]-PAPS and the crude enzyme at a certain temperature, was digested with a mixed solution containing heparitinase I, II, III shown below at 37° C. for 2 hours (50 μl containing 25 nmol or less of reaction product, 50 mM Tris-HCl (pH 7.2), 1 mM CaCl$_2$, 2 μg bovine serum albumin (BSA), 5 mU heparitinase I, 0.5 mU heparitinase II, 5 mU heparitinase III).

The digest was separated together with standard unsaturated disaccharides using HPLC (high speed liquid chromatography, column: silica column with bound polyamine (PAMN column)) in accordance with a known method (Habuchi, H. et al., (1992) *Biochem. J.*, 285, 805–813), fractionated into each aliquot of 0.6 ml, and mixed with 3 ml of liquid scintillator (Ready Safe Scintillator, produced by Beckman) to measure radioactivity by using a liquid scintillation counter. Heparitinase is an enzyme which cuts α-N-acetyl/-sulfo-D-glucosaminyl (1→4) uronic acid bond of heparan sulfate in a manner of an elimination reaction to produce oligosaccharides having $\Delta^4$-hexuronic acid at non-reducing end.

Results are shown in FIG. 1 (A: CHO cell, B: FM3A cell). In FIG. 1, reference numerals 1–5 indicate unsaturated disaccharide residues shown below (see formula 1 and Table 2). "ΔDiHS" indicates unsaturated disaccharide produced by degradation of heparin by heparitinase. "6,N" indicates a position of sulfation of glucosamine. "U" indicates the fact that C-2 of uronic acid is sulfated.

1: ΔDiHS-6S
2: ΔDiHS-NS
3: ΔDiHS-di(6,N)S
4: ΔDiHS-di(U,N)S
5: ΔDiHS-tri(U,6,N)S

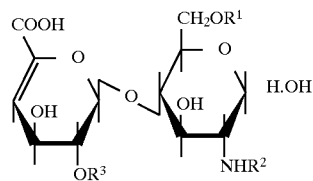

(1)

TABLE 2

| Unsaturated disaccharide residue | $R^1$ | $R^2$ | $R^3$ |
|---|---|---|---|
| ΔDiHS-6S | $SO_3^-$ | Ac | H |
| ΔDiHS-NS | H | $SO_3^-$ | H |
| ΔDiHS-di(6,N)S | $SO_3^-$ | $SO_3^-$ | H |
| ΔDiHS-di(U,N)S | H | $SO_3^-$ | $SO_3^-$ |
| ΔDiHS-tri(U,6,N)S | $SO_3^-$ | $SO_3^-$ | $SO_3^-$ |

As clarified from FIG. 1, the unsaturated disaccharide components produced by heparitinase digestion of CDSNS-heparin having sulfate group transferred from [$^{35}$S]-PAPS dominantly included ΔDiHS-di(6,N)S, however, ΔDiHS-di(U,N)S was contained in a trace amount. According to the result, it has been clarified that most of the heparan sulfate sulfotransferase activity produced and secreted by CHO cell is the heparan sulfate 6-sulfotransferase activity, scarcely containing the iduronic acid 2-sulfotransferase activity.

<3> Purification of heparan sulfate 6-sulfotransferase produced by CHO cell (1) Cultivation of CHO cell and preparation of culture liquid fractions CHO cell (ATCC CCL61) were inoculated in a roller bottle (produced by In vitro Science Product INC.) at a density of $3.3 \times 10^7$ cells/bottle, and cultivated for 2 days in 100 ml of Dulbecco's Modified Eagle Medium containing 10% fetal bovine serum, 10 mM HEPES, pH 7.2, 50 units/ml of penicillin, and 50 μg/ml of streptomycin. Subsequently, using 100 ml of Cosmedium-001 medium containing 50 μg/ml of ascorbic acid and 10 mM HEPES, pH 7.2, the culture liquid was recovered every second day, and a fresh medium was added to continue cultivation.

The cultivation was continued for 10 days. The recovered culture liquid was collected, and centrifuged at 1000×g for 5 minutes to remove floating cells. $MgCl_2$, $CaCl_2$, Tris-HCl, pH 7.2, glycerol, and Triton X-100 were added to the supernatant to give 10 mM, 2 mM, 10 mM, 20%, and 0.1% respectively to provide a buffered culture liquid, and it was stored at −20° C. until purification of the enzyme was started.

(2) Purification of heparan sulfate 6-sulfotransferase

All of the following operations were performed at 4° C.

(i) First step: first Heparin-Sepharose CL-6B chromatography

The buffered culture liquid (16 L) prepared as described above was applied to a Heparin-Sepharose CL-6B column (20×65 mm, 20 ml) equilibrated with buffer A (10 mM Tris-HCl, pH 7.2, 10 mM $MgCl_2$, 2 mM $CaCl_2$, 20% glycerol, 0.1% Triton X-100) containing 0.15M NaCl after dividing it into 10 aliquots. The flow rate was 70 ml/hour. A fraction not absorbed to the column was washed with buffer A containing 0.25M NaCl in an amount ten times the column volume, and then an absorbed fraction was eluted with buffer A containing 1M NaCl in an amount five times the column volume. The same operation was repeated ten times. Each of eluates were combined, and introduced into a dialysis tube to which powder of polyethylene glycol #20,000 was sprinkled to be left at 4° C., and thus it was concentrated to 100 ml. This concentrated solution was exhaustively dialyzed against buffer A containing 0.05M NaCl.

Owing to the operation described above, the heparan sulfate 6-sulfotransferase activity increased about 1.6-fold. This may be caused by elimination of degradation enzymes for PAPS and inhibiting substances for heparan sulfate 6-sulfotransferase activity through the column chromatography.

(ii) Second step: 3',5'-ADP-agarose chromatography

The dialyzed solution obtained in the first step described above was applied to a 3',5'-ADP-agarose column (14×90 mm, 15 ml) equilibrated with buffer A containing 0.05M NaCl after dividing it into 2 aliquots. The flow rate was 13 ml/hour. A fraction not absorbed to the column was washed with buffer A containing 0.05M NaCl in an amount eight times the column volume, and then an absorbed fraction was eluted with a linear concentration gradient for the 3',5'-ADP concentration increasing from 0 to 0.2 mM in buffer A containing 0.05M NaCl (total volume: 150 ml). It was found that the heparan sulfate 6-sulfotransferase was unstable in 0.05M NaCl, and hence buffer A containing 1M NaCl was added beforehand to test tubes for collecting each of fractions so that the final concentration of NaCl became 0.15M.

Figure 2:
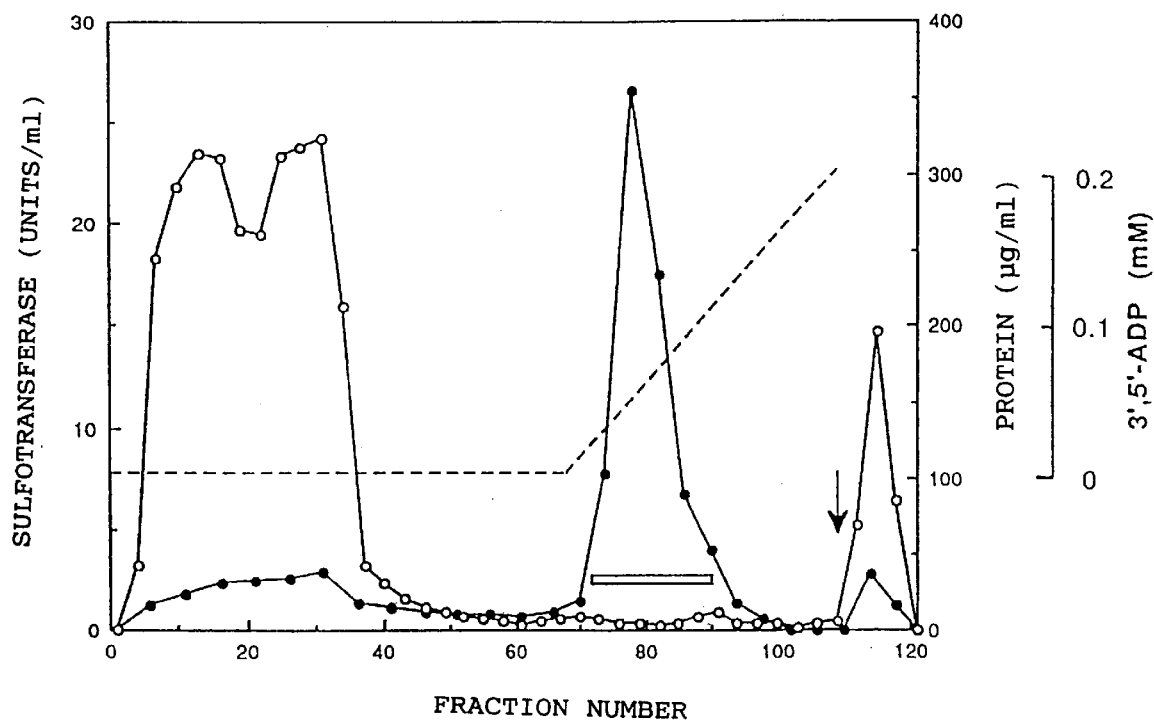
FIG. 2 shows a result of 3',5'-ADP-agarose chromatography for the enzyme of the present invention, wherein closed circles indicate heparan sulfate 6-sulfotransferase activity, open circles indicate protein concentration, and a broken line indicates 3',5'-ADP concentration.

The protein concentration and the heparan sulfate 6-sulfotransferase activity of each of eluted fractions were measured. The protein concentration was measured with a BCA kit (Pierce) using BSA (bovine serum albumin) as a standard. A result is shown in FIG. 2. Active fractions (portion shown by a thick line in FIG. 2) were collected. A part of the eluted solution was applied to a small Heparin-Sepharose column, washed with buffer A containing 0.25M NaCl, and then eluted with buffer A containing 1.0M NaCl. The activity of this fraction was measured to determine a total activity of the enzyme purified in this step.

Owing to the operation described above, the specific activity of heparan sulfate 6-sulfotransferase became 35-fold at a stroke, revealing that the operation was an extremely effective method for purification of this enzyme.

(iii) Third step: second Heparin-Sepharose CL-6B chromatography

The active fraction of the heparan sulfate 6-sulfotransferase obtained in the second step was applied to a Heparin-Sepharose CL-6B column (16×35 mm, 5 ml) equilibrated with buffer A containing 0.15M NaCl. The column was washed with buffer A containing 0.25M NaCl in an amount five times the column volume, and then an absorbed fraction was eluted with a linear concentration gradient of the NaCl concentration increasing from 0.25M to 1.2M in the buffer (total volume: 150 ml). The protein concentration, the heparan sulfate 6-sulfotransferase activity, and the chondroitin sulfotransferase activity of each of eluted fractions were measured.

Figure 3:
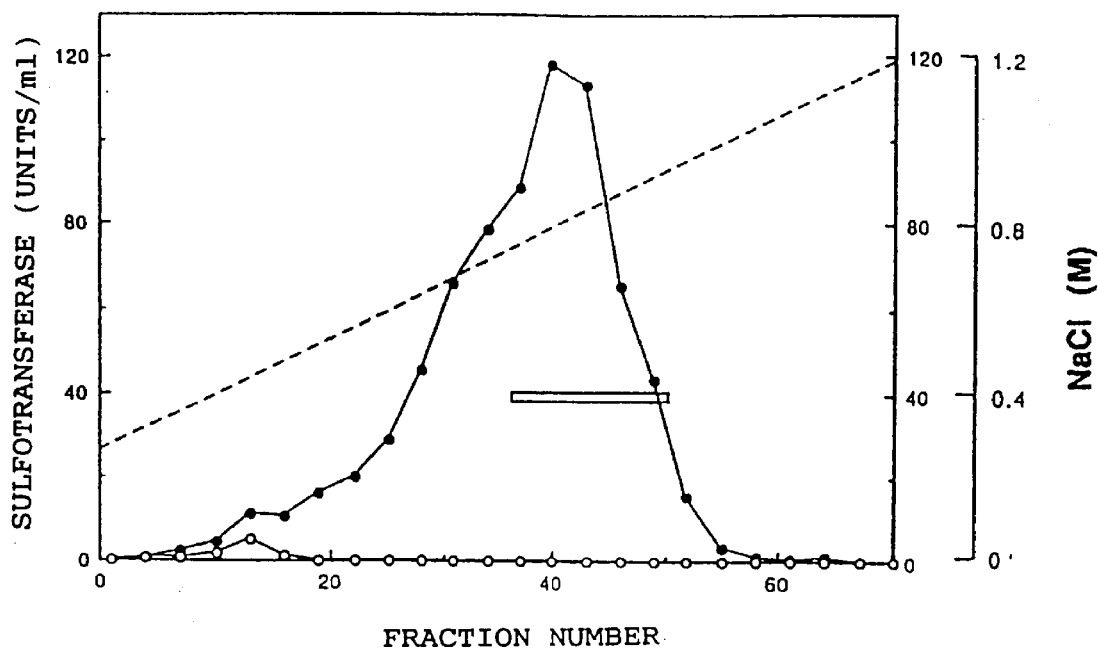
FIG. 3 shows a result of second Heparin-Sepharose CL-6B chromatography for the enzyme of the present invention, wherein closed circles indicate heparan sulfate 6-sulfotransferase activity, open circles indicate chondroitin sulfotransferase activity, and a broken line indicates NaCl concentration.

A result is shown in FIG. 3. Chondroitin sulfotransferase was eluted at a salt concentration lower than that of heparan sulfate 6-sulfotransferase, and it was eliminated in this step. The chondroitin sulfotransferase transferred sulfate group to C-4 of N-acetylgalactosamine in chondroitin or chondroitin sulfate, but it did not transfer sulfate group to C-6 of N-acetylgalactosamine.

Among the fractions containing the heparan sulfate 6-sulfotransferase activity obtained as described above, fractions shown by a thick line in FIG. 3 were collected, and dialyzed against buffer A containing 0.15 M NaCl. The purified enzyme thus obtained was stored at −20° C.

Figure 4:
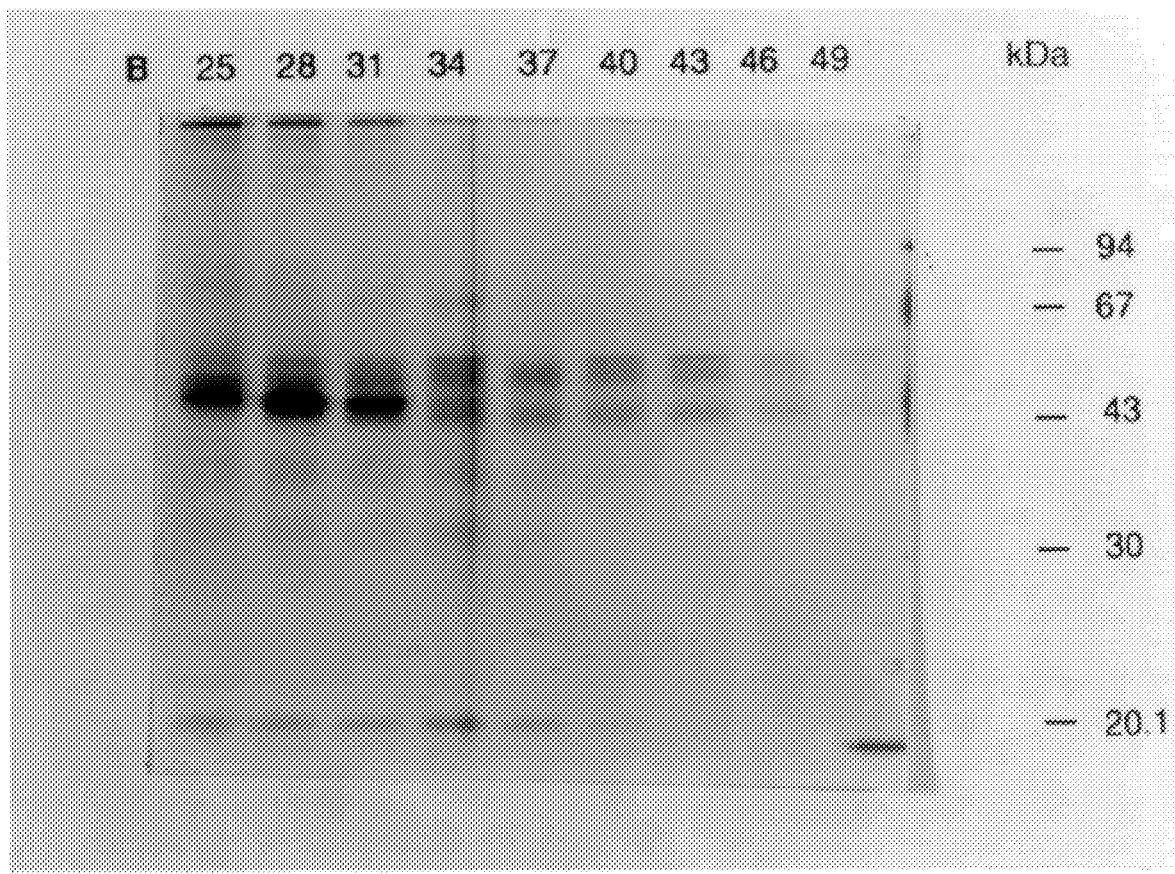
FIG. 4 shows a result of SDS-polyacrylamide gel electrophoresis for fractions fractionated by second Heparin-Sepharose CL-6B chromatography, wherein numbers at the top of the figure indicate fraction numbers.

As described above, the heparan sulfate 6-sulfotransferase was purified about 10,700-fold from the buffered culture liquid, and it gave approximately homogeneous two bands on SDS-PAGE as described below (FIG. 4). The degree of purification in each of the steps is shown in Table 3.

TABLE 3

| Purification step | Volume ml | Total activity × $10^3$ U | Total protein mg | Specific activity × $10^4$ U/mg | Purification degree-fold | Yield (%) |
| --- | --- | --- | --- | --- | --- | --- |
| buffered culture liq. | 16,000 | 5.99 | 718 | 0.000834 | 1 | 100 |
| 1st Heparin-Sepharose | 1,000 | 9.78 | 76 | 0.0129 | 16 | 163 |
| 3',5'-ADP-agarose | 140 | 5.40 | 1.25 | 0.433 | 519 | 90 |
| 2nd Heparin-Sepharose | 35 | 2.38 | 0.027 | 8.94 | 10,700 | 40 |

(3) Analysis of purified enzyme by SDS-polyacrylamide gel electrophoresis

Figure 5:
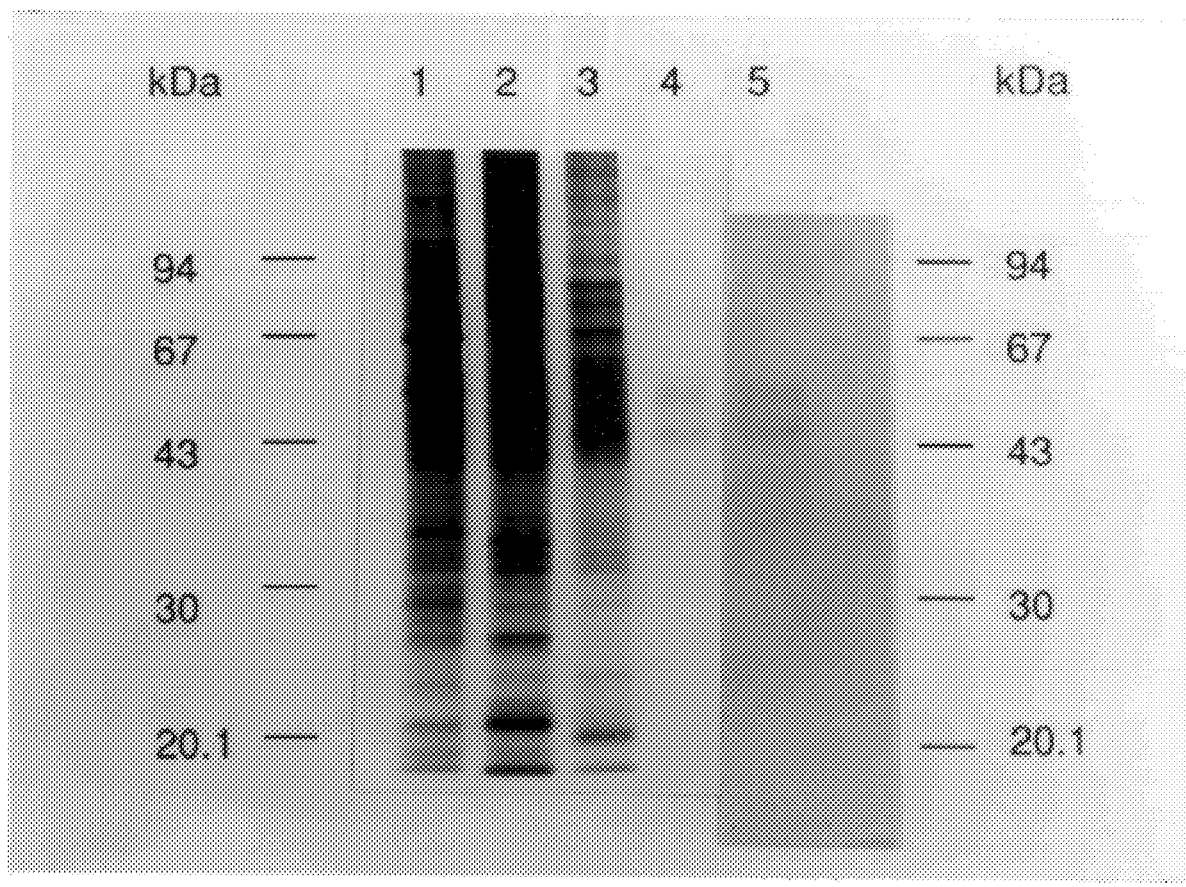
FIG. 5 shows a result of SDS-polyacrylamide gel electrophoresis for enzyme fractions of the present invention in each of purification steps and purified enzyme treated with 5% mercaptoethanol, wherein lane 1 is buffered culture liquid components, lane 2 is an absorbed fraction of first Heparin-Sepharose CL-6B, lane 3 is an absorbed fraction of 3',5'-ADP-agarose, lane 4 is fractions of a portion of a horizontal line (thick line) shown in FIG. 3 in second Heparin-Sepharose CL-6B chromatography, and lane 5 is the same fractions as those in lane 4 but reduced with 5% mercaptoethanol.

The purified enzyme of heparan sulfate 6-sulfotransferase and samples in each of the steps of purification obtained as described above were analyzed by SDS-polyacrylamide gel electrophoresis by using 10% gel in accordance with Laemmli (Laemmli, U. K. (1970) *Nature*, 227, 680–685). Bands of proteins were detected by silver staining or Coomassie Brilliant Blue staining. A result is shown in FIG. 5. Two bands of 52 kDa and 45 kDa were dominantly observed by silver staining in the second Heparin-Sepharose fraction. This fraction was reduced with 5% mercaptoethanol, and stained with Coomassie Brilliant Blue, which is shown in lane 5 in FIG. 5. No change in molecular weight of the two bands was observed between those before and after the reduction.

Next, it was investigated whether or not the sugar chain was present in the heparan sulfate 6-sulfotransferase protein. The enzyme protein was precipitated by adding TCA (trichloroacetic acid) to a heparan sulfate 6-sulfotransferase solution containing 0.15 µg of the protein so that the final concentration was 10%. The precipitate was recovered by centrifugation. The precipitate was washed with acetone and dried, and then kept at a temperature of 37° C. for 16 hours in a reaction solution described below.

The reaction solution contained 0.05M Tris-HCl, pH 7.8 containing 0.5% SDS (10 µl); 7.5% (w/v) Nonidet P-40 (5 µl); 0.25M EDTA (1.2 µl); phenylmethylsulfonylfluoride (0.3 µl); and 0.5 unit of N-glycanase (recombinant N-glycanase: produced by Genzyme).

Figure 6:
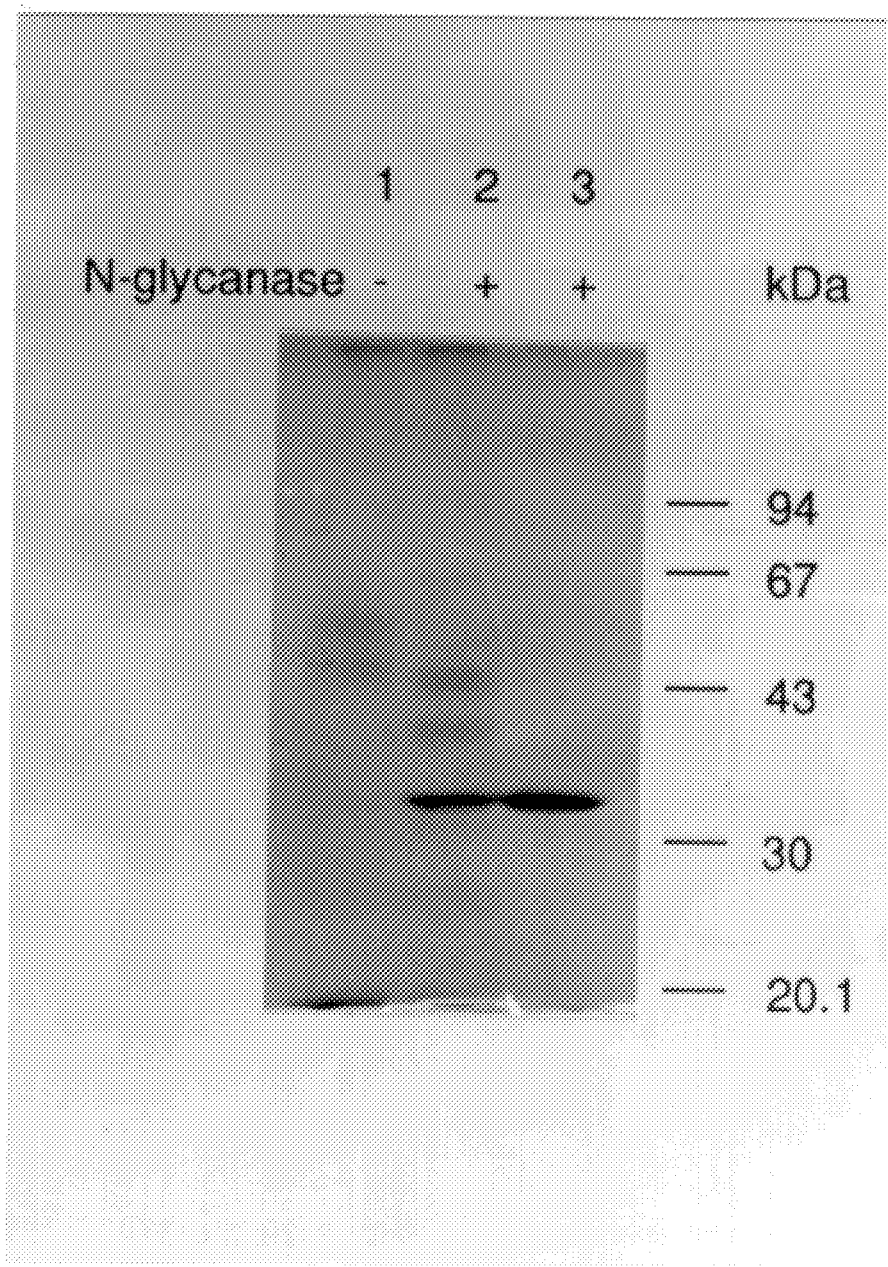
FIG. 6 shows a result of SDS-polyacrylamide gel electrophoresis of the enzyme of the present invention treated with or without N-glycanase (produced by Genzyme Co.), wherein lane 1 is the enzyme of the present invention with no treatment, lane 2 is the enzyme of the present invention treated with N-glycanase, and lane 3 is N-glycanase.

As a result of analysis of the reaction solution described above by means of SDS-PAGE, the protein bands of 52 kDa and 45 kDa disappeared, and protein bands of 43 kDa and 38 kDa appeared (FIG. 6). This result demonstrates that the proteins of the both bands are glycoproteins containing more than 15% of sugar.

(4) N-terminal amino acid analysis of heparan sulfate 6-sulfotransferase

In order to determine amino acid sequences at N-terminals of the purified heparan sulfate 6-sulfotransferase, the proteins were transferred from the gel to a PVDF (polyvinylidene difluoride) membrane (Applied Biosystems) by electroblot at 40 V for 16 hours in 10 mM CAPS (cyclohexylaminopropanesulfonic acid) buffer (10 mM CAPS containing 10% methanol, pH 11). Amino acid sequences of samples of the enzyme proteins blotted to the PVDF membrane were determined by using a gas phase sequencer.

As a result, a sequence of 16 residues at the N-terminal was clarified for the protein of 45 kDa, demonstrating that it was a region rich in proline. This fact well coincides with the knowledge that a stem domain of sugar transferase of Golgi body is generally rich in proline. On the other hand, the band of 52 kDa had a sequence coincided with the sequence of 45 kDa except for 3 residues which could not be identified among 11 residues. Thus the two bands are considered to be proteins extremely relevant to one another.

The amino acid sequences at the N-terminals of the proteins of 45 kDa and 52 kDa are shown in SEQ ID NOS. 1 and 2, respectively. In SEQ ID NO. 1, it is extremely probable that 6th amino acid is Leu or Ala, 11th amino acid is Pro or Ala, and 14th amino acid is Arg or Phe. Although 9th, 12th, 13th, 15th and 16th amino acids are uncertain, amino acid having high possibility are shown. Also in SEQ ID NO. 2, although 2th, 6th, and 9th to 11th amino acids are uncertain, amino acid having high possibility are shown.

(5) Substrate specificity of heparan sulfate 6-sulfotransferase

In order to investigate the substrate specificity of the heparan sulfate 6-sulfotransferase of the present invention, the activity to transfer $^{35}$S-sulfate group from [$^{35}$S]-PAPS was measured by using the crude enzyme or the purified enzyme using various substrates (25 nmol) as acceptors. Results are shown in Table 4. Numbers in parentheses in the table indicate the activity to transfer sulfate group with respect to each of the acceptors when the activity to transfer sulfate group using CDSNS-heparin as the acceptor is regarded to be 100.

TABLE 4

| Substrate | Crude enzyme activity, U/ml | Purified enzyme activity, U/ml |
| --- | --- | --- |
| CDSNS-heparin | 11.2 (100) | 74.2 (100) |
| heparan sulfate | 3.46 (31) | 26.0 (35) |
| chondroitin | 1.42 (13) | 0 |
| chondroitin-4-sulfate | 0.08 (0.7) | 0 |
| NDS-heparin | 0.72 (6.0) | 1.7 (2.3) |

The heparan sulfate 6-sulfotransferase of the present invention transferred sulfate group to CDSNS-heparin and heparan sulfate (originating from swine aorta), and transferred sulfate group to NDS-heparin (N-desulfated heparin) a little. However, no transfer was observed in chondroitin and chondroitin-4-sulfate.

Figure 7:
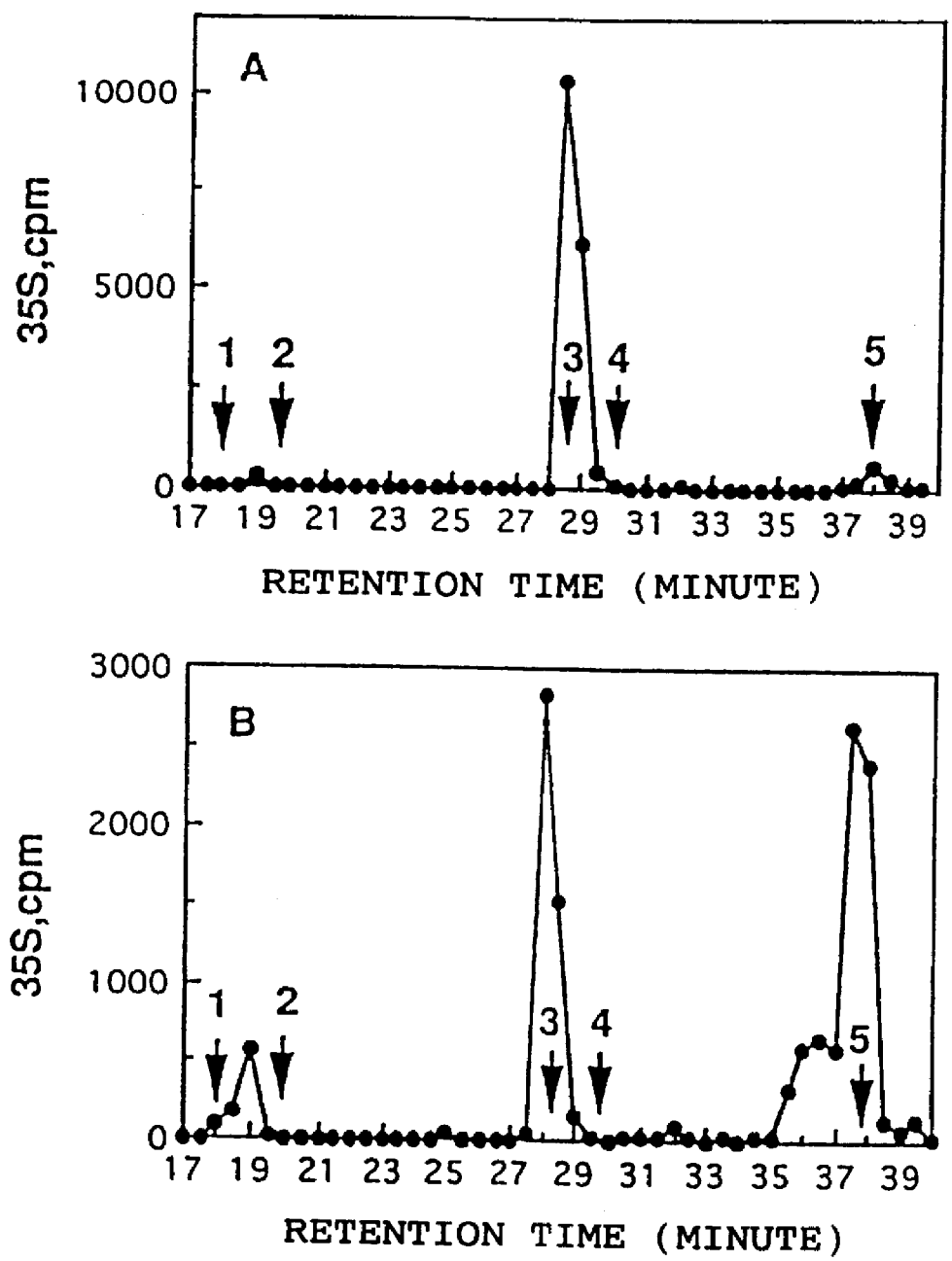
FIG. 7 shows HPLC chromatograms of heparitinase digests of products of the reaction to transfer sulfate group to CDSNS-heparin (A) and heparan sulfate (B) by the enzyme of the present invention.

In order to investigate the position of sulfate group transferred by the heparan sulfate 6-sulfotransferase of the present invention using CDSNS-heparin and heparan sulfate as acceptors and using [$^{35}$S]-PAPS as a sulfate group donor, transfer reaction products were digested with heparitinase in the same manner as described above, and analyzed by HPLC using a PAMN column. Results are shown in FIG. 7. Reference numerals in the figure are the same as those in FIG. 1.

As a result, when CDSNS-heparin was used as an acceptor, almost all of the radioactivity coincided with the elution position of standard ΔDiHS-di(6,N)S, however, a little amount of radioactivity was also present at the position of ΔDiHS-tri(U,6,N)S (FIG. 7A). On the other hand, when heparan sulfate was used as an acceptor, the radioactivity was present in approximately equal amounts at the positions of ΔDiHS-di(6,N)S and ΔDiHS-tri(U,6,N)S (FIG. 7B). When heparan sulfate was used as an acceptor, the content of the peak 5 is high as compared with the case of CDSNS-heparin. This may be caused by the fact that the content of units having sulfate group at C-2 of uronic acid in heparan sulfate used for the reaction is higher than that of CDSNS-heparin.

These results demonstrate that the heparan sulfate 6-sulfotransferase of the present invention has the activity to transfer sulfate group to C-6 of N-sulfoglucosamine existing in glycosaminoglycan, the acceptor of sulfate group probably serving well even when adjacent hexuronic acid is sulfated or not sulfated.

Figure 8:
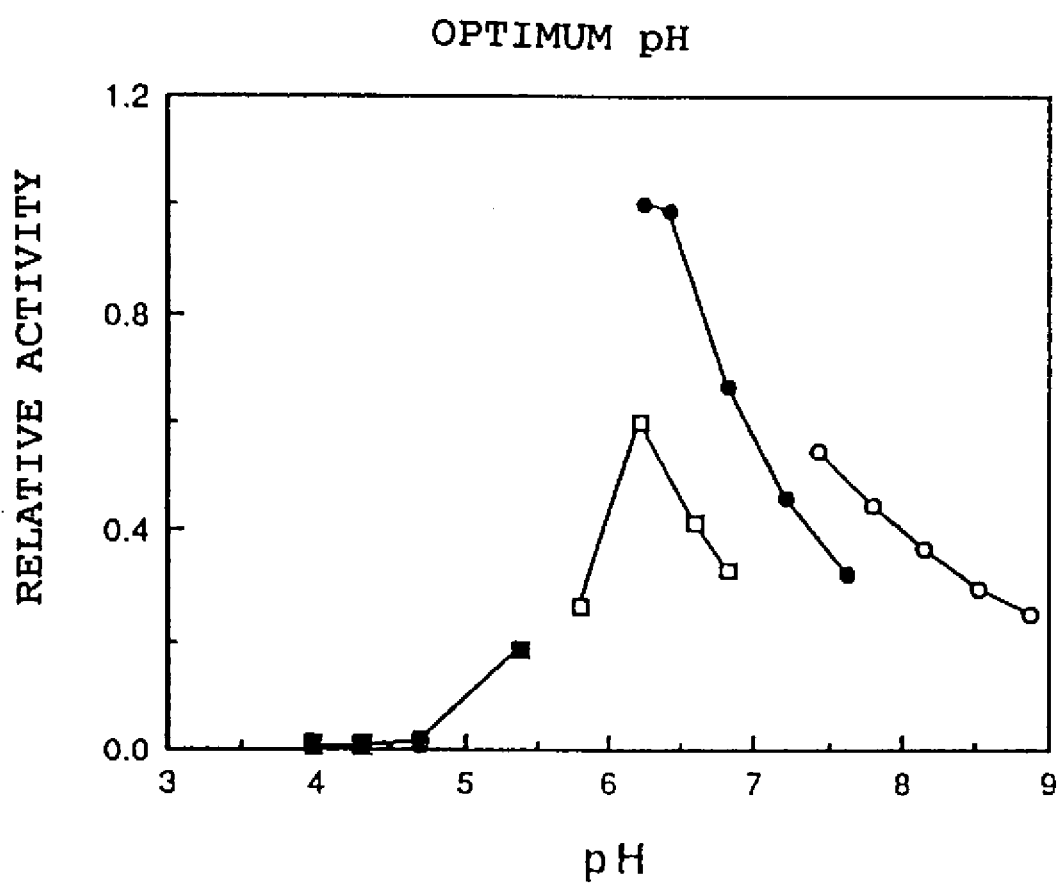
FIG. 8 shows pH-enzyme activity curves demonstrating optimum pH of the enzyme of the present invention, wherein open circles indicate Tris-HCl buffer, closed circles indicate imidazole-HCl buffer, open squares indicate MES buffer, and closed squares indicate potassium acetate buffer.

(6) Other enzymatic properties of heparan sulfate 6-sulfotransferase (i) Optimum pH Optimum pH of the enzyme of the present invention was measured. Buffers that were 50 mM Tris-HCl, 50 mM imidazole-HCl, 50 mM MES (2-(N-morpholino)ethanesulfonic acid, produced by nacalai tesque), and 50 mM potassium acetate buffer were used. The enzyme activity was measured at various pH's. Relative activities with respect to an activity in imidazole-HCl buffer (pH 6.3) are respectively shown in FIG. 8. As a result, a maximum activity was obtained at about pH 6.3.

(ii) Inhibition and activation of the enzyme of the present invention

Figure 9:
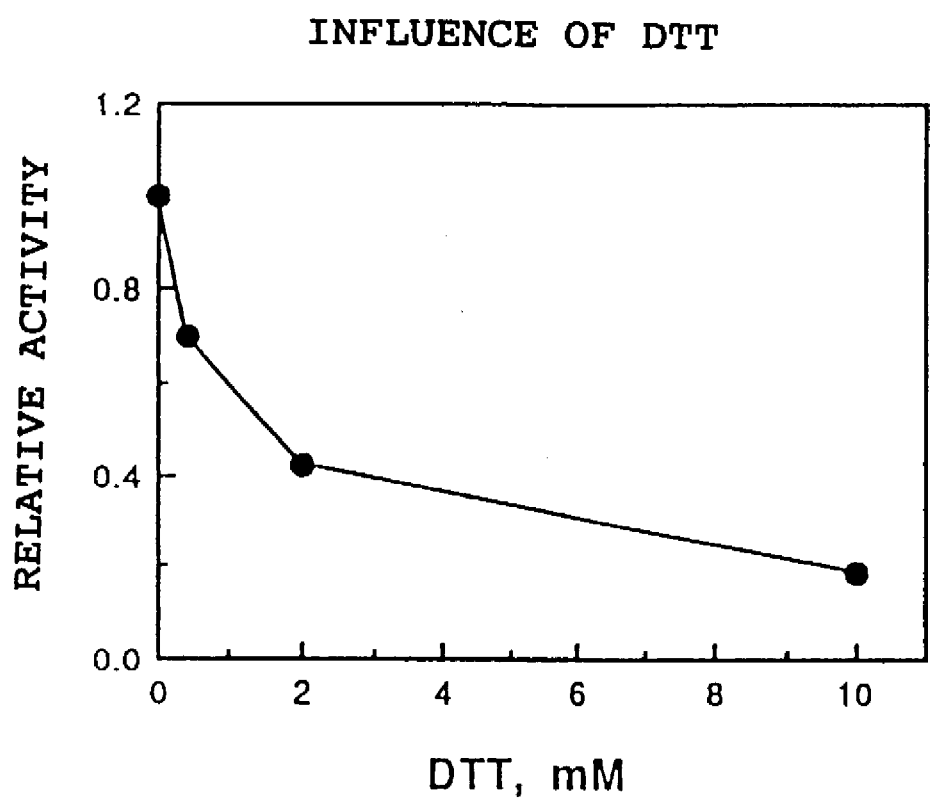
FIG. 9 shows a DTT concentration-enzyme activity curve showing the influence of DTT on the enzyme of the present invention.

In order to investigate the influence of dithiothreitol (DTT) and protamine on the activity of the enzyme of the present invention, DTT or protamine was added to a reaction solution at various concentrations to measure the enzyme activity. The relative activity with respect to the activity without addition of DTT is shown in FIG. 9. DTT inhibited the enzyme activity as the concentration increases. The enzyme activity decreased to 42% at 2 mM DTT and to 19% at 10 mM DTT.

Figure 10:
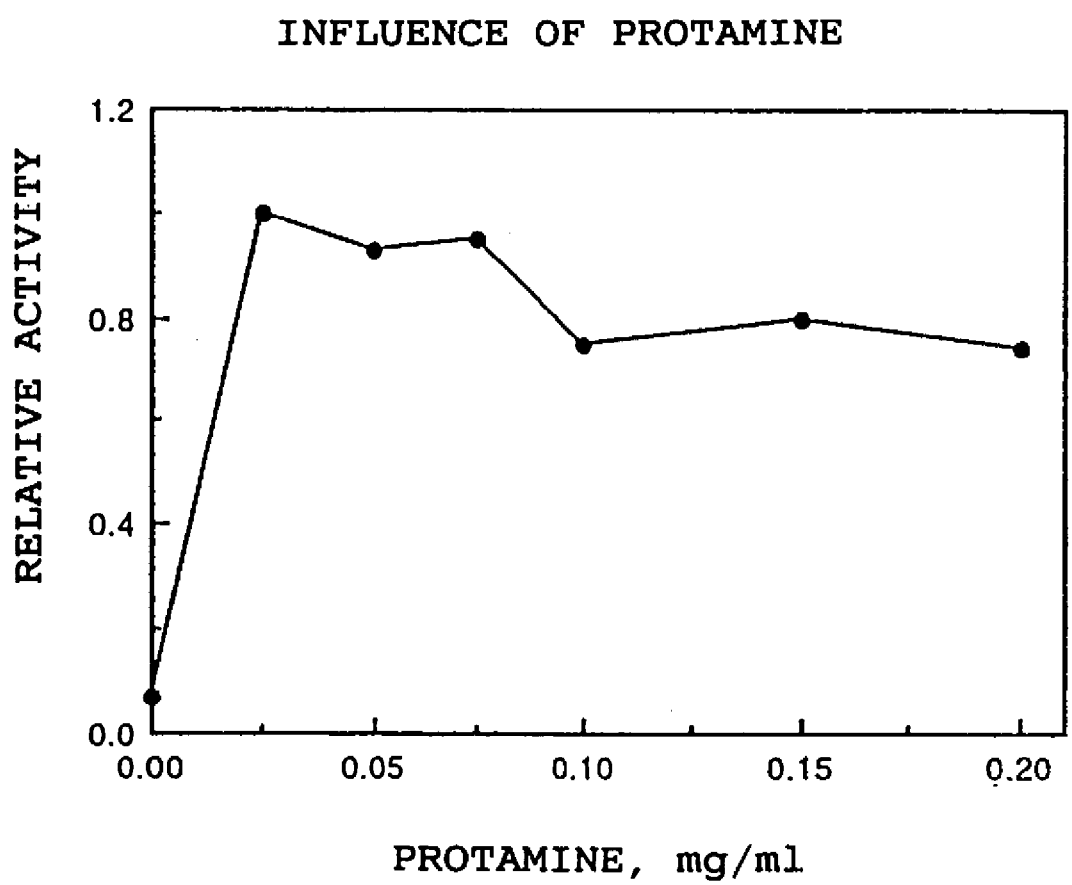
FIG. 10 shows a protamine concentration-enzyme activity curve showing the influence of protamine on the enzyme of the present invention.

The influence of protamine on the enzyme activity of the enzyme of the present invention was investigated. The relative activity with respect to the maximum activity is shown in FIG. 10. The heparan sulfate 6-sulfotransferase was remarkably activated by protamine in the same manner as chondroitin 4-sulfotransferase and chondroitin 6-sulfotransferase.

Figure 11:
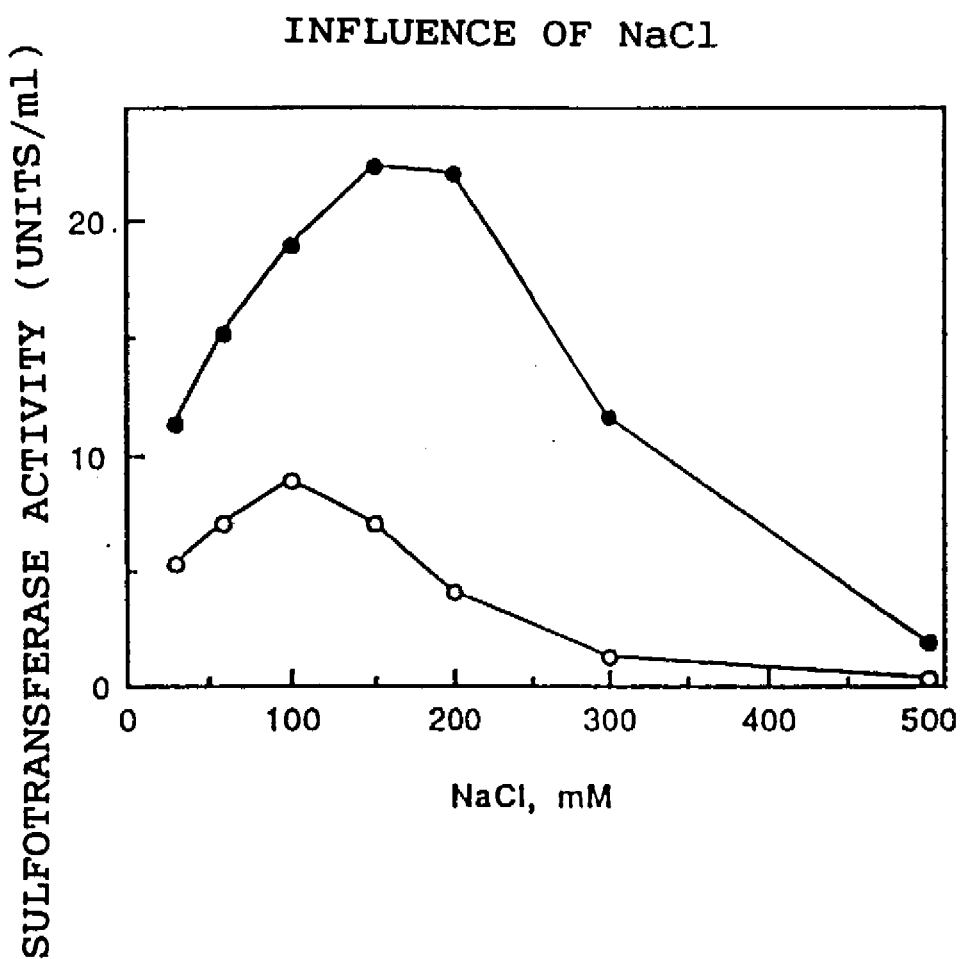
FIG. 11 shows an NaCl concentration-enzyme activity curve showing optimum NaCl concentration of the enzyme of the present invention, wherein closed circles indicate no addition of DTT, and open circles indicate addition of 2 mM DTT.

Next, the influence of NaCl on the enzyme activity was investigated. NaCl was added to an enzyme reaction solution at various concentrations in the presence or absence of DTT. Results are shown in FIG. 11. The maximum activity was observed at about 150 mM NaCl without addition of DTT, and at about 100 mM NaCl with addition of 2 mM DTT. This property is different from that of N-sulfotransferase in which the activity is inhibited depending on the concentration of NaCl.

As a result of investigation of the influence of 3',5'-ADP on the enzyme activity of the enzyme of the present invention, a strong inhibiting action was found in the same manner as other sulfotransferases.

(iii) Measurement of Michaelis constant

Figure 12:
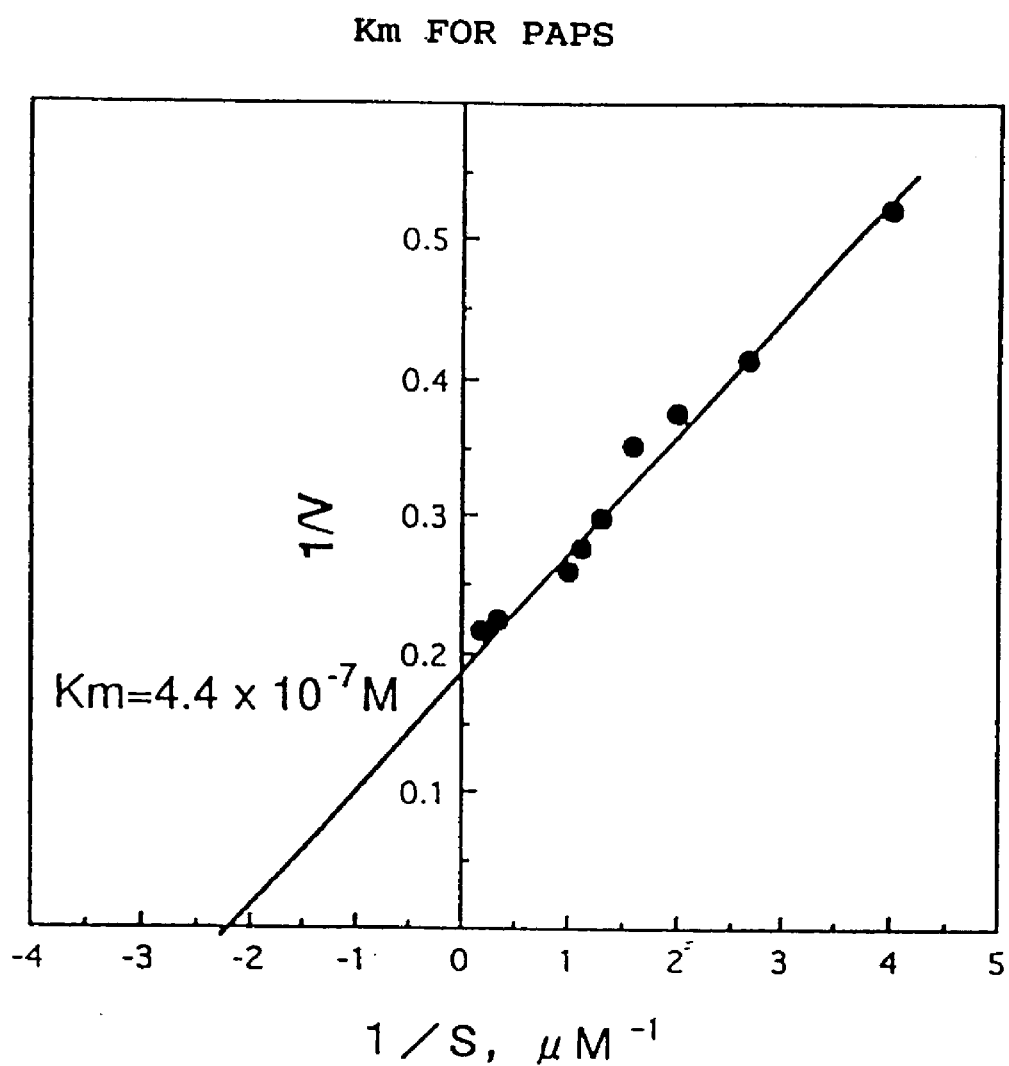
FIG. 12 shows a Lineweaver-Burk plot for calculating Km of the enzyme of the present invention.

Michaelis constant (Km) was determined for the enzyme of the present invention when heparan sulfate was used as a sulfate group acceptor and PAPS was used as a donor. PAPS (0.125–5 μM) was added to 50 μl of a reaction solution containing 0.19 unit of the enzyme and 25 nmol of CDSNS-heparin as hexosamine, and reacted at 37° C. for 20 minutes to measure initial velocities of the reaction. A Lineweaver-Burk plot was prepared (see FIG. 12), and Michaelis constant was calculated. As a result, Km of the enzyme of the present invention for PAPS was $4.4 \times 10^{-7}$M.

---

What is claimed is:

1. A heparan sulfate 6-O-sulfotransferase having the following physical and chemical properties:
   (i) action: sulfate group is transferred from a sulfate group donor selectively to the hydroxyl group position at C-6 of N-sulfoglucosamine residue in heparin or heparan sulfate, but not significantly to the position of the hydroxyl group at C-2 of glucuronic acid or iduronic acid residue in heparin or heparan sulfate;
   (ii) substrate specificity: sulfate group is transferred to heparan sulfate or CDSNS-heparin, but sulfate group is not transferred to chondroitin and chondroitin-4-sulfate;
   (iii) optimum reaction Ph: Ph 6–7
   (iv) optimum ionic strength: 0.1–0.3M when sodium chloride is used; and
   (v) inhibition and activation: the enzyme is inhibited by dithiothreitol and adenosine-3',5'-diphosphate, and the activity of the enzyme is increased by protamine.

2. A heparan sulfate 6-O-sulfotransferase according to claim 1, wherein said sulfate group donor is 3'-phosphoadenosine 5'-phosphosulfate.

3. A method of producing heparan sulfate 6-O-sulfotransferase, comprising the steps of:
   cultivating cells of at least one cell line selected from the group consisting of CHO cell line ATCC CCL61, FM3A cell line, and MG63 cell line ATCC CRL1427, in a culture medium, whereby the heparan sulfate 6-O-sulfotransferase defined in claim 1 is secreted in the medium,
   recovering the resultant medium, and
   isolating and purifying the heparan sulfate 6-O-sulfotransferase from said medium.

4. A heparan sulfate 6-O-sulfotransferase according to claim 1, which has been increased in activity by protamine.

5. A heparan sulfate 6-O-sulfotransferase according to claim 1, which has an N-terminal amino acid sequence as shown in SEQ ID No. 1 or SEQ ID NO. 2.

6. A heparan sulfate 6-O-sulfotransferase according to claim 1, which has a molecular weight of about 45 kDa or about 52 kDa determined by SDS-polyacrylamide gel electrophoresis.

7. A heparan sulfate 6-O-sulfotransferase according to claim 1, which is a glycoprotein.

8. A heparan sulfate 6-O-sulfotransferase according to claim 1, which has only the 6-O-sulfotransferase activity.

9. A method of producing heparan sulfate 6-O-sulfotransferase according to claim 3, wherein said cell line is CHO cell line.

10. A method of producing heparan sulfate 6-O-sulfotransferase according to claim 3, wherein the isolating and purifying step comprises purification by 3',5'-ADP-agarose column chromatography.

11. A method of producing heparan sulfate 6-O-sulfotransferase according to claim 3, wherein the medium is a serum-free medium.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal (v) ORIGINAL SOURCE:

(xi) SEQUENCE DESCRIPTION: SEQ ID NO:1:

| Leu | Pro | Gly | Pro | Arg | Xaa | Pro | Leu | Gly | Ala | Xaa | Leu | Leu | Xaa | Ala | Pro |
|---|---|---|---|---|---|---|---|---|---|---|---|---|---|---|---|
| 1 | | | | 5 | | | | | 10 | | | | | 15 | |

(2) INFORMATION FOR SEQ ID NO:2:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:2:

| Xaa | Pro | Gly | Pro | Xaa | Leu | Xaa | Leu | Gly | Ala | Pro |
|---|---|---|---|---|---|---|---|---|---|---|
| 1 | | | | 5 | | | | | 10 | |